United States Patent
Choi et al.

(10) Patent No.: US 10,472,678 B2
(45) Date of Patent: Nov. 12, 2019

(54) REAGENT FOR DETECTING CROSS CONTAMINATION OF PDX-MODEL RELATED WITH HUMAN AND MOUSE, THE KIT COMPRISING THE SAME, AND THE METHOD FOR THE CROSS CONTAMINATION DETECTION

(71) Applicant: Abion Inc, Seoul (KR)

(72) Inventors: Yoon La Choi, Seoul (KR); Yun Su Lee, Bucheon-si (KR)

(73) Assignee: ABION INC, Seoul (KR)

( * ) Notice: Subject to any disclaimer, the term of this patent is extended or adjusted under 35 U.S.C. 154(b) by 40 days.

(21) Appl. No.: 15/582,773

(22) Filed: May 1, 2017

(65) Prior Publication Data

US 2017/0321275 A1 Nov. 9, 2017

(30) Foreign Application Priority Data

May 3, 2016 (KR) ........................ 10-2016-0054458

(51) Int. Cl.
*C12Q 1/68* (2018.01)
*C07H 21/04* (2006.01)
*C12Q 1/6881* (2018.01)

(52) U.S. Cl.
CPC ..... *C12Q 1/6881* (2013.01); *C12Q 2600/158* (2013.01)

(58) Field of Classification Search
None
See application file for complete search history.

(56) References Cited

U.S. PATENT DOCUMENTS

2015/0253340 A1 9/2015 Altiok

FOREIGN PATENT DOCUMENTS

| JP | 2007209281 A | 8/2007 |
| JP | 2012175928 A | 9/2012 |
| KR | 1020140133399 A | 11/2014 |

*Primary Examiner* — Katherine D Salmon
(74) *Attorney, Agent, or Firm* — STIP Law Group, LLC

(57) ABSTRACT

The present application relates to a detection kit for genotypes capable of confirming cross contamination that may occur in a banking process of a patient-derived xenograft model or cell-derived xenograft model and a method for determining cross contamination using the same. According to the present invention, it is possible to determine all of cross contamination of mouse related genes, have high detection sensitivity and specificity to be close to 100%, rapidly examine the contamination, and be very useful in predicting mouse contamination.

Therefore, according to the present invention, cross contamination of genes related with the human and the mouse is predicted in advance to be applied to evaluation of anticancer drug efficacy using a patient-derived xenograft model or cell-derived xenograft model and contribute to cell banks using the patient-derived xenograft model or cell-derived xenograft model, and as a result, the present invention is very useful in a medical industry.

6 Claims, 15 Drawing Sheets

Specification includes a Sequence Listing.

[FIG. 1]
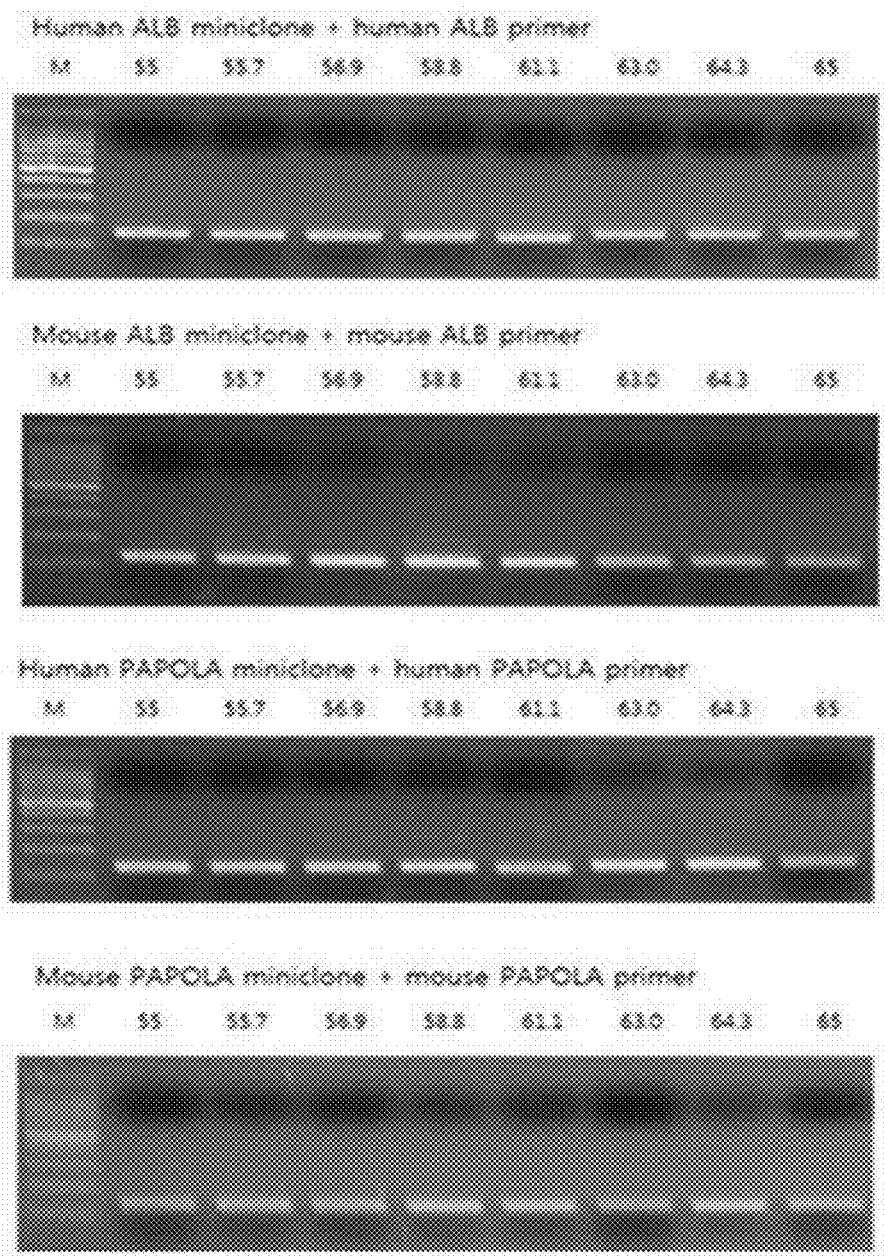

[FIG. 2]
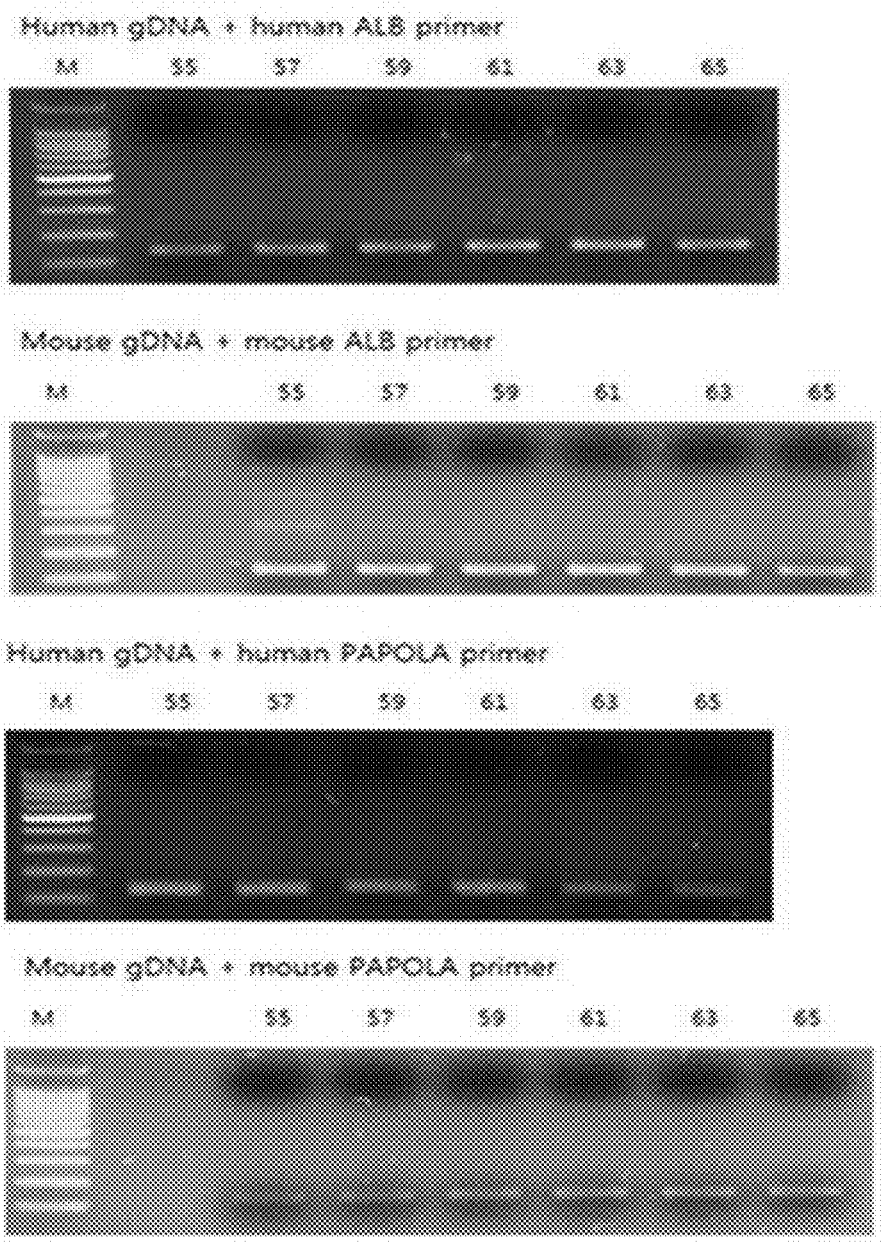

[FIG. 3]
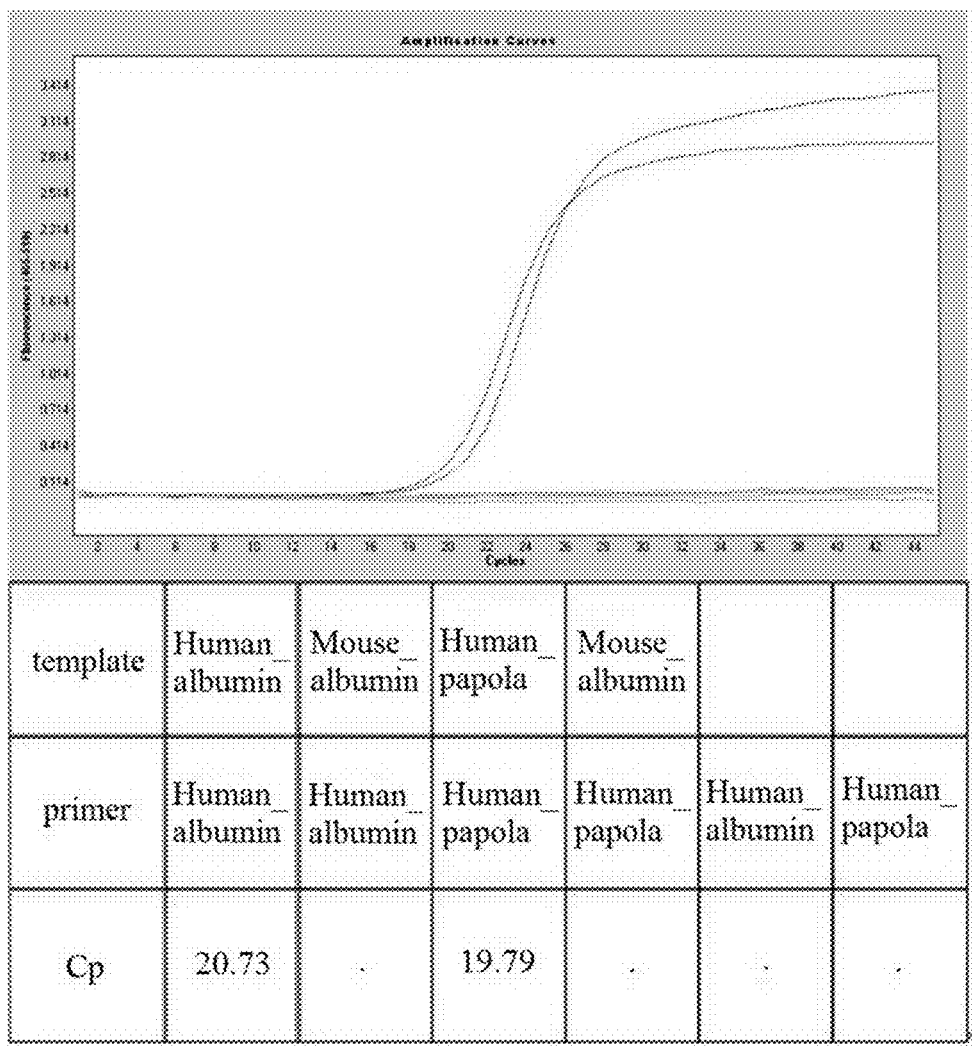

[FIG. 4]
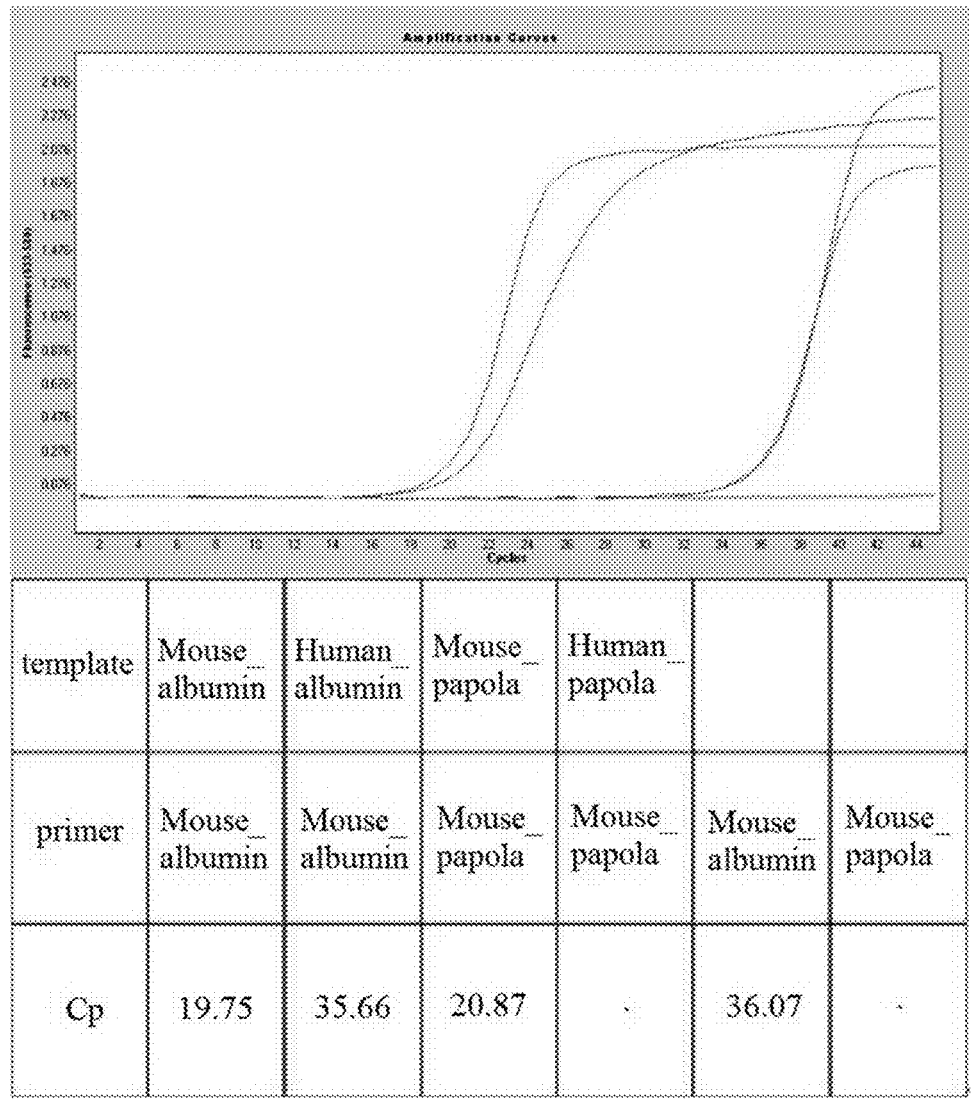

[FIG. 5]
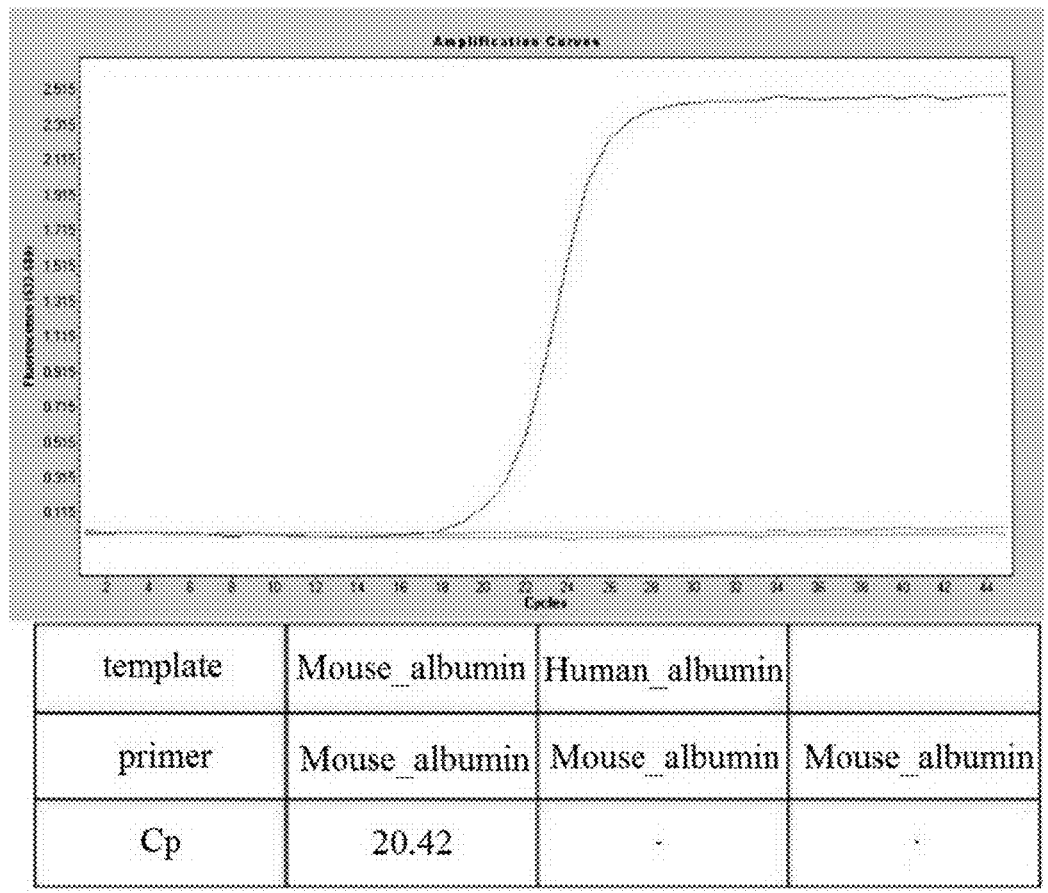

[FIG. 6]
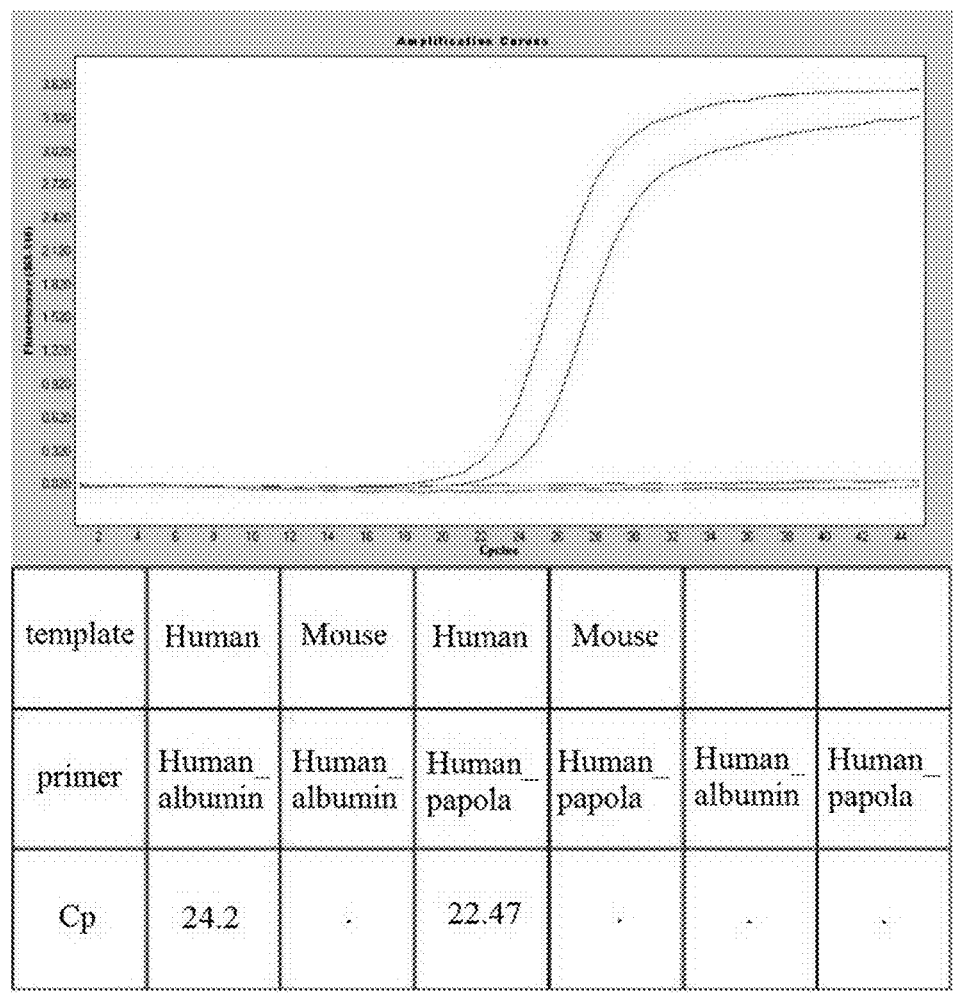

[FIG. 7]
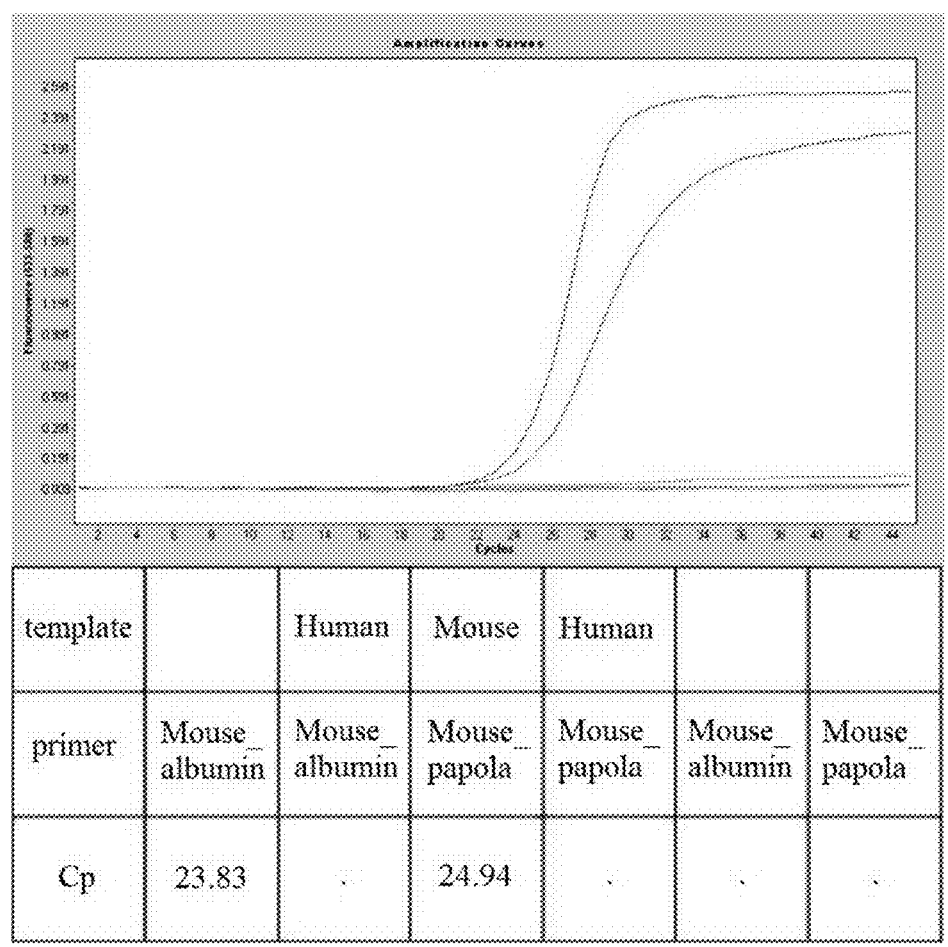

[FIG. 8]
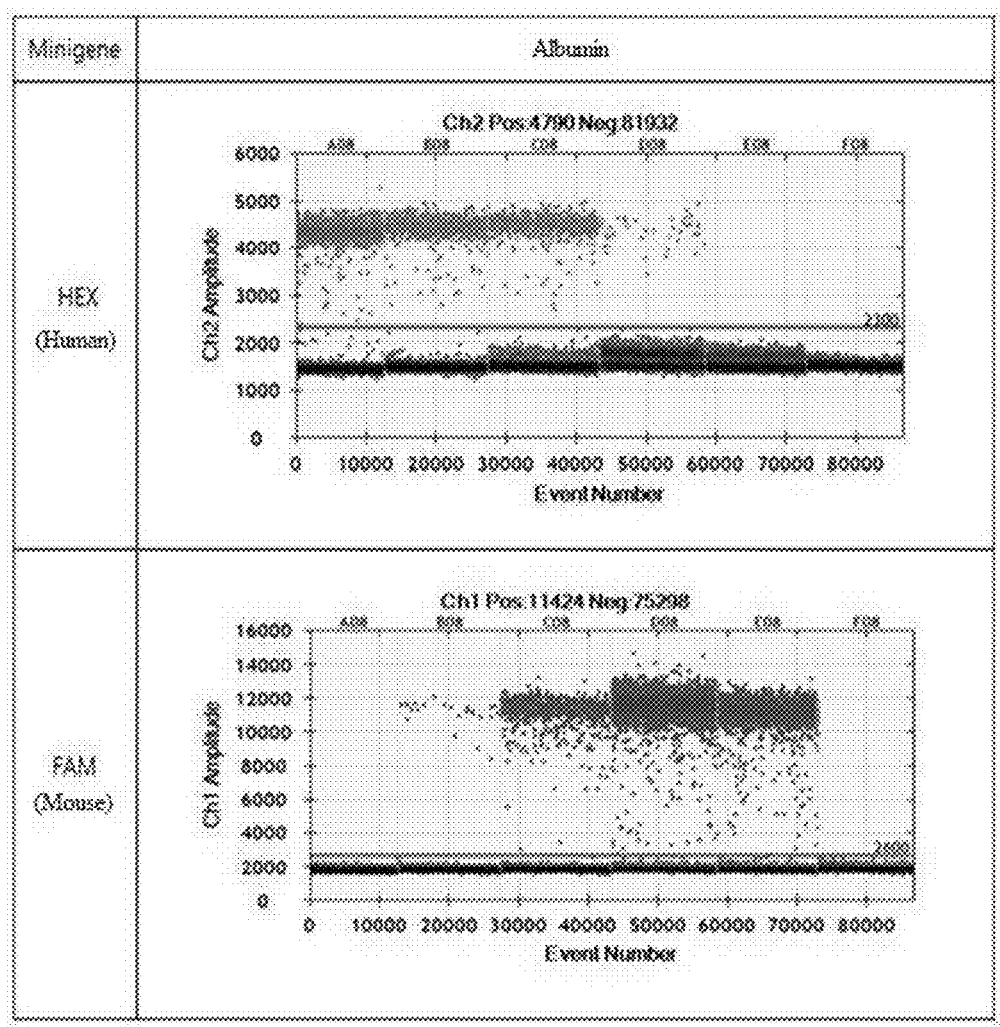

[FIG. 9]
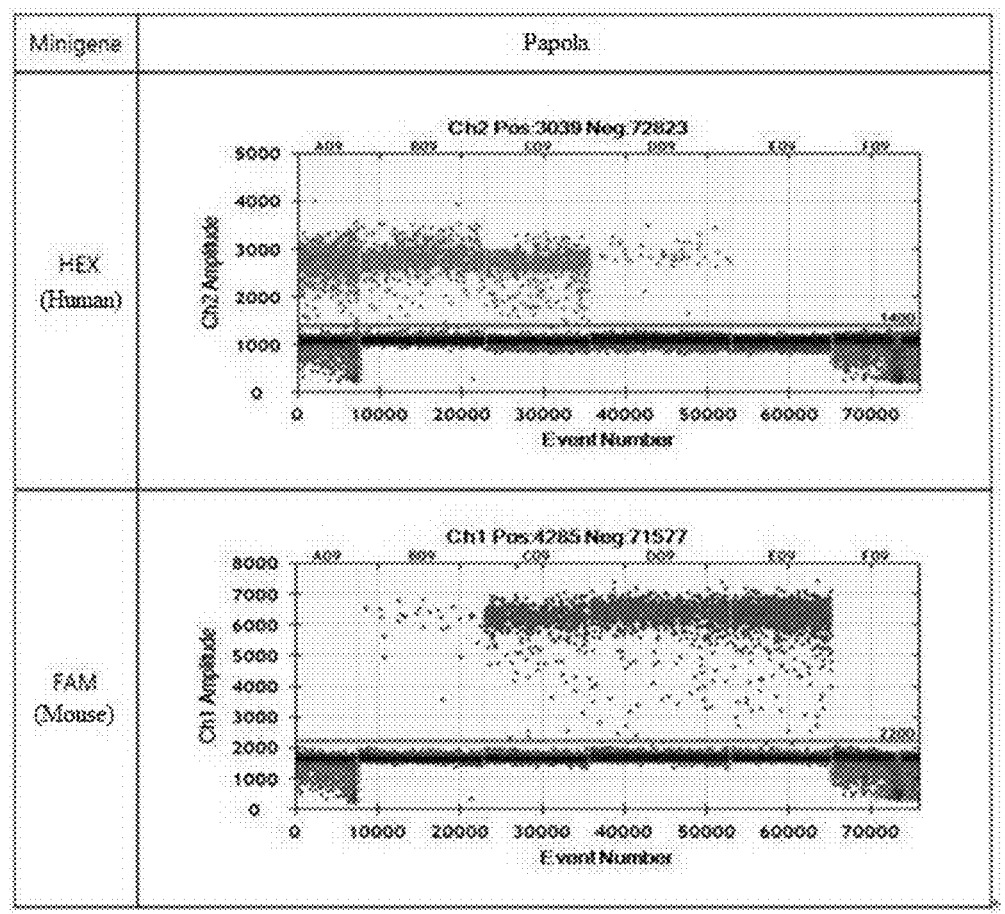

[FIG. 10]
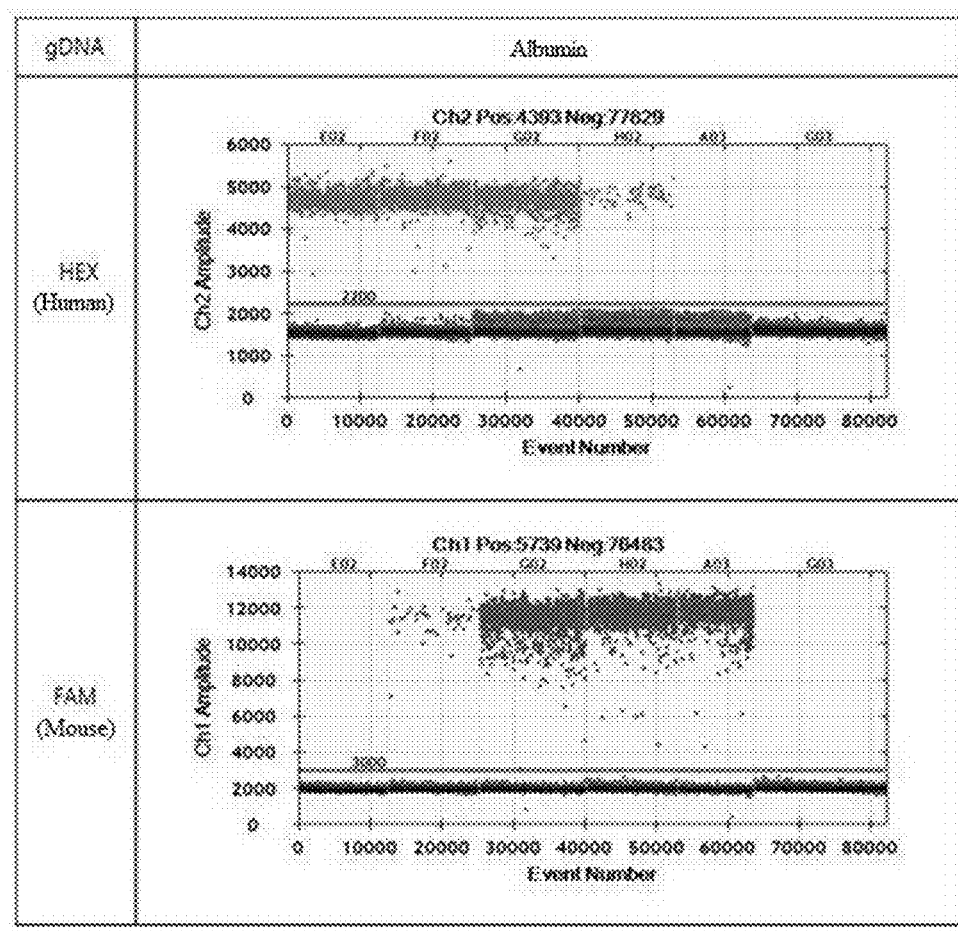

[FIG. 11]
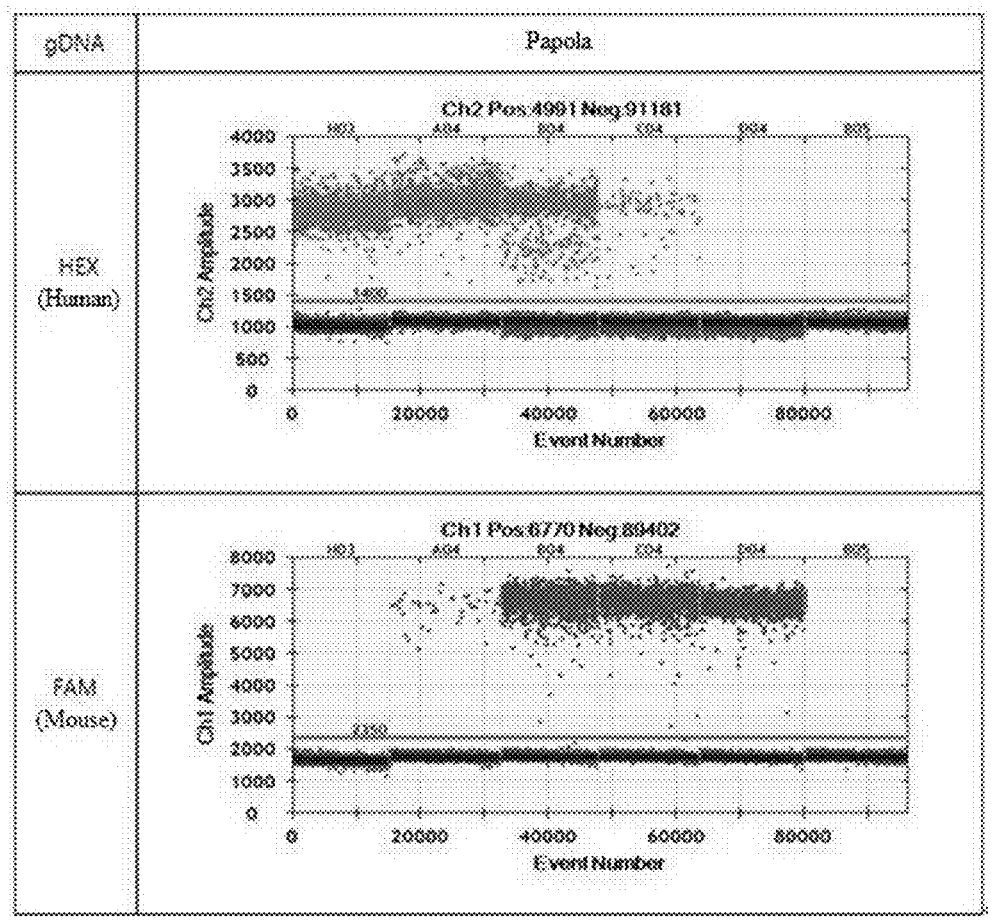

[FIG. 12]
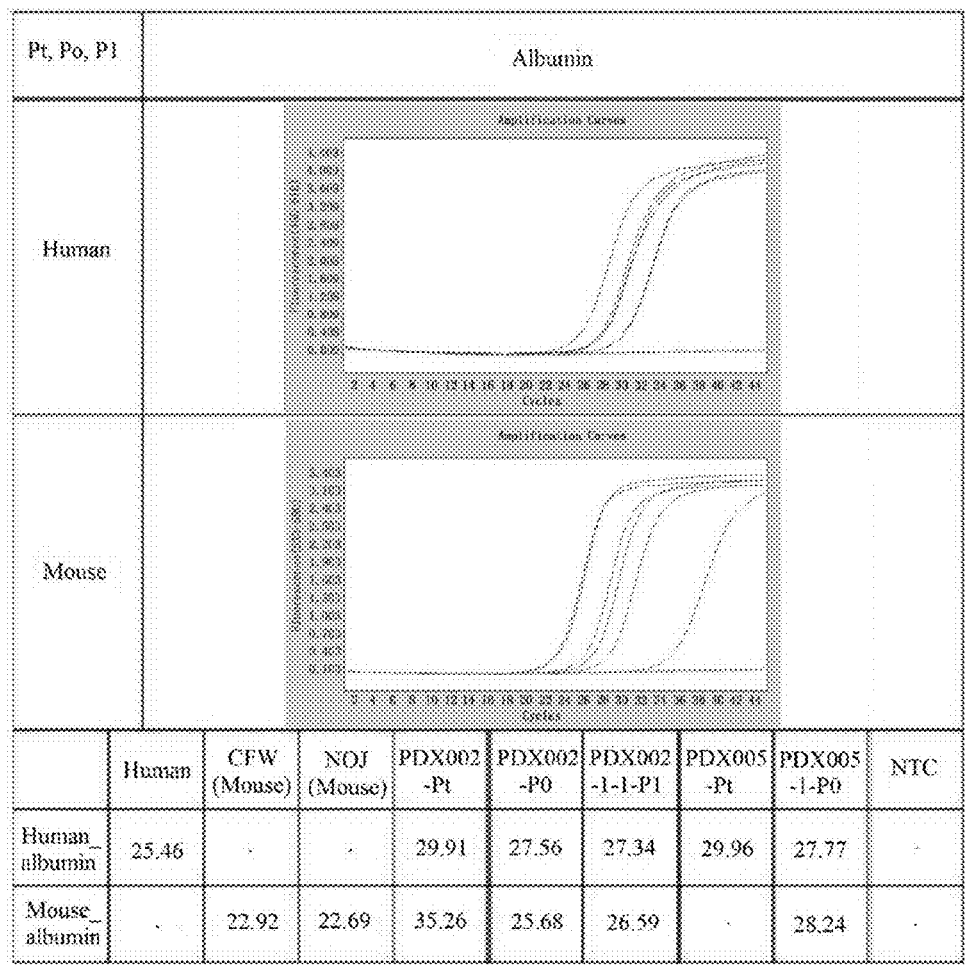

[FIG. 13]
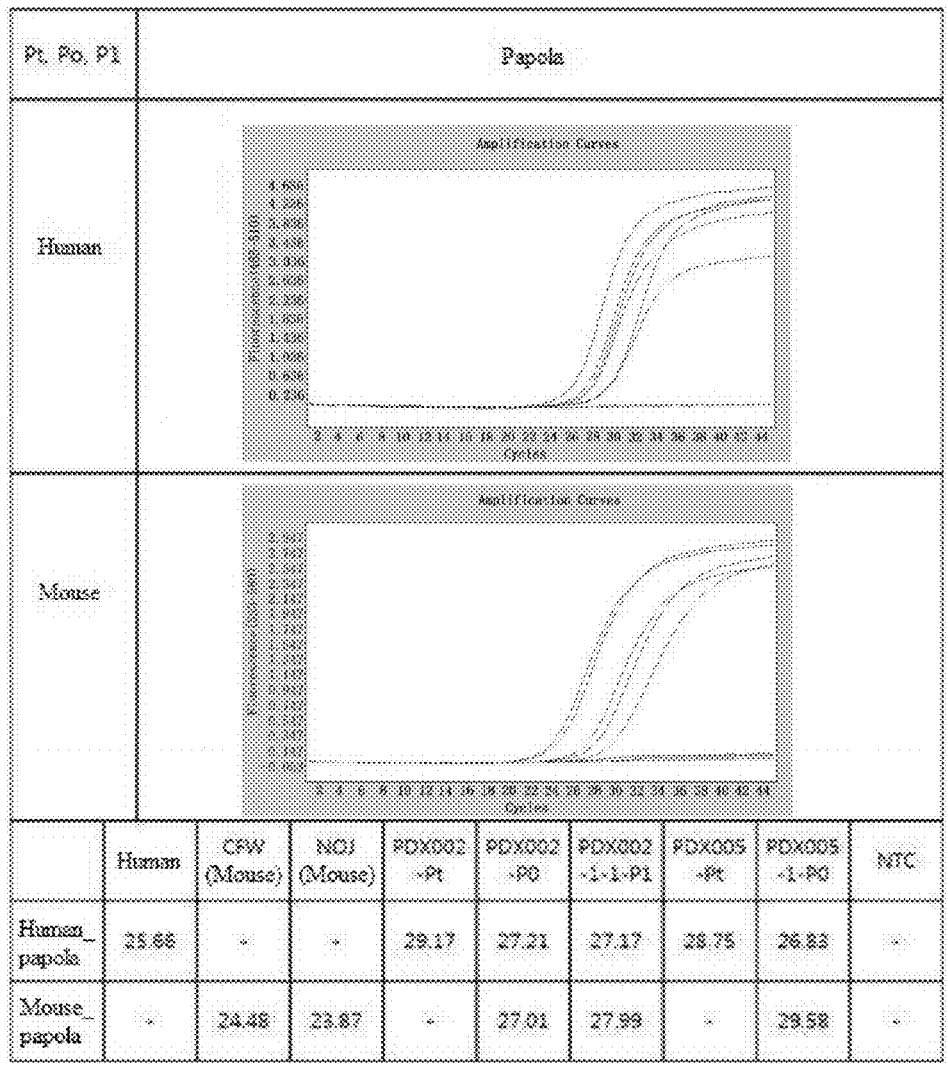

[FIG. 14]

| Pt, Po, P1 | Albumin | | | | |
|---|---|---|---|---|---|
| HEX (Human) | Ch2 Pos 638 Neg 97684 graph | | | | |
| FAM (Mouse) | Ch1 Pos 438 Neg 97875 graph | | | | |
| PDX samples | | HEX (Human) | | FAM (Mouse) | |
| | | Conc. (copies/μL) | caculated copies | Conc. (copies/μL) | caculated copies |
| PDX002-Pt | Albumin | 4.2 | 84 | 0 | 0 |
| PDX002-1-P0 | | 14.4 | 288 | 20.5 | 410 |
| PDX002-1-1-P1 | | 19.8 | 396 | 10.4 | 208 |
| PDX005-Pt | | 5.1 | 102 | 0 | 0 |
| PDX005-1-P0 | | 16.8 | 336 | 3.4 | 68 |

[FIG. 15]
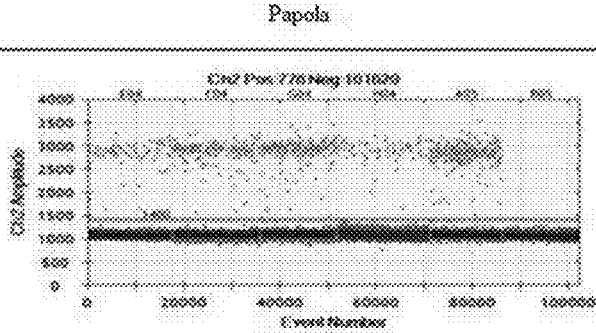

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthesized

<400> SEQUENCE: 1
ggtctgagga gaaagtgtag ca                                             22

<210> SEQ ID NO 2
<211> LENGTH: 22
<212> TYPE: DNA
<213> ORGANISM: Artificial Sequence
<220> FEATURE:
<223> OTHER INFORMATION: Synthesized

<400> SEQUENCE: 2
cagaggtttt tcacagcatt cc                                             22

<210> SEQ ID NO 3
<211> LENGTH: 21
<212> TYPE: DNA
<213> ORGANISM: Artificial Sequence
<220> FEATURE:
<223> OTHER INFORMATION: Synthesized

<400> SEQUENCE: 3
gattgataaa gccagggtga t                                              21

<210> SEQ ID NO 4
<211> LENGTH: 22
<212> TYPE: DNA
<213> ORGANISM: Artificial Sequence
<220> FEATURE:
<223> OTHER INFORMATION: Synthesized

<400> SEQUENCE: 4
actgtcactg tcactgtcaa gc                                             22

<210> SEQ ID NO 5
<211> LENGTH: 22
<212> TYPE: DNA
<213> ORGANISM: Artificial Sequence
<220> FEATURE:
<223> OTHER INFORMATION: Synthesized
```

```
<400> SEQUENCE: 5
cgttaggata tgtggtaagc gt                                              22

<210> SEQ ID NO 6
<211> LENGTH: 22
<212> TYPE: DNA
<213> ORGANISM: Artificial Sequence
<220> FEATURE:
<223> OTHER INFORMATION: Synthesized

<400> SEQUENCE: 6
ataaacgcat ccattacctc ca                                              22

<210> SEQ ID NO 7
<211> LENGTH: 22
<212> TYPE: DNA
<213> ORGANISM: Artificial Sequence
<220> FEATURE:
<223> OTHER INFORMATION: Synthesized

<400> SEQUENCE: 7
ttcctgggtc aaggttactt ag                                              22

<210> SEQ ID NO 8
<211> LENGTH: 22
<212> TYPE: DNA
<213> ORGANISM: Artificial Sequence
<220> FEATURE:
<223> OTHER INFORMATION: Synthesized

<400> SEQUENCE: 8
aaagtgatcg ccagattcaa tg                                              22

<210> SEQ ID NO 9
<211> LENGTH: 25
<212> TYPE: DNA
<213> ORGANISM: Artificial Sequence
<220> FEATURE:
<223> OTHER INFORMATION: Synthesized

<400> SEQUENCE: 9
ccaacttact tataggcgga ccttg                                           25

<210> SEQ ID NO 10
<211> LENGTH: 25
<212> TYPE: DNA
<213> ORGANISM: Artificial Sequence
<220> FEATURE:
<223> OTHER INFORMATION: Synthesized

<400> SEQUENCE: 10
aaagtctcac cacatgactg cccaa                                           25

<210> SEQ ID NO 11
<211> LENGTH: 25
<212> TYPE: DNA
<213> ORGANISM: Artificial Sequence
<220> FEATURE:
<223> OTHER INFORMATION: Synthesized

<400> SEQUENCE: 11
aggttgcgtg ctcttatggc agaaa                                           25

<210> SEQ ID NO 12
```

```
<211> LENGTH: 25
<212> TYPE: DNA
<213> ORGANISM: Artificial Sequence
<220> FEATURE:
<223> OTHER INFORMATION: Synthesized

<400> SEQUENCE: 12
tgtttcttat gcctccatag gtggt                                                25
```

REAGENT FOR DETECTING CROSS CONTAMINATION OF PDX-MODEL RELATED WITH HUMAN AND MOUSE, THE KIT COMPRISING THE SAME, AND THE METHOD FOR THE CROSS CONTAMINATION DETECTION

CROSS-REFERENCE TO RELATED APPLICATIONS

This application claims the priority of Korean Patent Application No. 10-2016-0054458 filed on May 3, 2016, in the Korean Intellectual Property Office, the disclosure of which is incorporated herein by reference.

SEQUENCE LISTING

A SEQUENCE LISTING is submitted in a file named pus170022_ST25 new.txt via EFS Web and is hereby incorporated by reference in its entirety. Said file was created on Jun. 14, 2017 and is 2,606 bytes in size.

BACKGROUND

Field

The present application relates to a method for measuring a ratio of a patient-derived stromal tumor and a mouse stromal tumor in a patient derived xenograft (PDX) model and analyzing an origin of cancer tissue or cell development because while generation of the xenograft model progresses, cancer tissues or cells of the human disappear and the stroma ratio of the human and the mouse varies according to conversion into the mouse stroma. More particularly, it relates to a analysis kit including primers and probes capable of detecting cross contamination of mouse and human genes and a method for analyzing cross contamination of the mouse gene for human cells using the same.

Description of the Related Art

Recently, researches for overcoming cancers through patient-specific anticancer therapy have been competitively conducted. A preclinical test that determines whether to enter clinical trials of novel therapeutic agents in a process of developing drugs for anticancer therapy is an important process for selecting therapeutic agents having high possibility of success. In this case, an ideal model to be used needs to satisfy various conditions, such as prediction for accurate therapeutic response, understanding of preceding target molecular pathway, preservation of histological, molecular, and cancer-ambient microenvironments that can represent actual clinical patients, and ease of pharmacokinetic or pharmacodynamic analysis. Currently, three main models of the preclinical test for the novel anticancer therapeutic agents include genetically engineered models, xenograft models derived from human tumor cell lines, and tumorgraft models derived from patients implanted directly into immunodeficient mice.

Over the past several decades, a xenograft model derived from a cell line panel representing various tumor species has been pointed out as a main limitation due to low predictability of success in actual clinical. In an alternative for overcoming the problem, patient-derived tumorgrafts (PDX) in which a patient-derived tumor tissue surgically removed is directly implanted into the immunodeficient mice are proposed. The patient derived xenograft (PDX) and cell derived xenograft (CDX) tumor models may provide clinical models required for new drug development, and the PDX model has been widely used in approaching new anticancer agents in the previous clinical studies because a clinical real situation of the patient may be summarized well in the mouse model. The PDX model is installed by implanting a surgically resected patient's tissue into immunodeficient mice and the xenografted tissue may be sequentially subcultured, kept in a freezer, and revived. In addition, it has been reported that while the patient-derived stroma which was initially maintained in the successive subculture is gradually replaced with the mouse stromal cells, the absolute amount thereof is decreased, but a relative cancer-to-stroma ratio is maintained. Through a comparison of gene expression profiles performed for the heterogeneous tissues in the early and late subcultures, a change in stroma characteristics may be inferred. Further, the change in stroma characteristics may be analyzed by separating cancer and cancer-ambient microenvironments through a selective gene expression array analysis in only the human and the mouse. Accordingly, by measuring the ratio of the patient-derived stromal tumors and the mouse stromal tumors in the patient-derived xenograft and cell-derived xenograft tumor models, while the patient-derived stroma that has been initially maintained in the successive subculture process is gradually replaced with the mouse stromal cells, a method for easily analyzing contamination of a mouse-derived tissue is required.

SUMMARY

The present application is directed to provide a detection kit capable of detecting cross contamination of human genes by measuring a ratio of patient-derived stromal tumors and mouse stromal tumors in a patient-derived xenograft model and a method for analyzing cross contamination of genes using the same.

The present invention provides a method for easily analyzing cross contamination of mouse-derived tissues shown while a patient-derived stroma that has been initially maintained in a successive subculture process of implanted tissues or cells is gradually replaced with mouse stromal cells, in a patient-derived xenograft model or cell-derived xenograft model. For example, the present application relates to a detection kit including primers and probes for measuring a ratio of patient-derived stromal tumors and mouse stromal tumors included in xenograft cells of a human and a mouse and can analyze cross contamination of the mouse-derived tissue using the detection kit. Particularly, the detection kit is very useful for rapidly, accurately, and automatically analyzing cross contamination of samples in the patient-derived xenograft model or cell-derived xenograft model and genotypes thereof. Further, according to the analyzing method, it is possible to determine cross contamination of genes related with the mouse and rapidly examine the cross contamination of the genes because sensitivity and specificity of the detection are high enough to be close to 100%.

A detection kit that determines patient-derived xenograft cells of the present application includes oligonucleotide primers consisting of base sequences of SEQ ID NOS: 1 to 4, and oligonucleotide probes consisting of base sequences of SEQ ID NOS: 9 and 10. For example, the oligonucleotide primers consisting of base sequences of SEQ ID NOS: 1 and 2 may be primers for amplifying a human albumin gene and the oligonucleotide primers consisting of base sequences of SEQ ID NOS: 3 and 4 may be primers for amplifying a mouse albumin gene. The oligonucleotide primers consisting of base sequences of SEQ ID NOS: 1 to 4 may complementarily bind to gene-specific sites to amplify the human albumin gene and the mouse albumin gene. Accordingly, it is possible to analyzing cross contamination of patient-derived xenograft cells by measuring a ratio of the human albumin genes and the mouse albumin genes included in the xenograft cells of the human and the mouse by using the detection kit including the oligonucleotide primers consisting of base sequences of SEQ ID NOS: 1 to 4 and the oligonucleotide probes consisting of base sequences of SEQ ID NOS: 9 and 10.

Further, the detection kit may determine a ratio of the genes included in the xenograft cells of the human and the mouse by using a labeling means that detects the amplified genes. In one example, the labeling means may be at least one selected from a group consisting of CY3, CY5, CY5.5, Bodipy, Alexa 488, Alexa 532, Alexa 546, Alexa 568, Alexa 594, Alexa 660, Rhodamine, TAMRA, FAM, FITC, Fluor X, ROX, Texas Red, Orange green 488X, Orange green 514X, HEX, TET, JOE, Oyster 556, Oyster 645, Bodipy 630/650, Bodipy 650/665m Calfluor Orange 546, Calfluor red 610, Quasar 670, HEX, VIC, BHQ, BHQ1, MGB, ZEN, and biotin, and preferably, may use FAM, HEX, MGB or BHQ1.

Another embodiment of the detection kit for determining the patient-derived xenograft cells of the present application may further include oligonucleotide primers consisting of base sequences of SEQ ID NOS: 5 to 8, and oligonucleotide probes consisting of base sequences of SEQ ID NOS: 11 and 12. For example, the oligonucleotide primers consisting of base sequences of SEQ ID NOS: 5 and 6 may be primers for amplifying a human papola gene and the oligonucleotide primers consisting of base sequences of SEQ ID NOS: 7 and 8 may be primers for amplifying a mouse papola gene. The oligonucleotide primers consisting of base sequences of SEQ ID NOS: 5 to 8 may complementarily bind to gene-specific sites to amplify the human papola gene and the mouse papola gene. Accordingly, it is possible to analyzing cross contamination of patient-derived xenograft cells by measuring a ratio of the human papola genes and the mouse papola genes included in the xenograft cells of the human and the mouse by using the detection kit including the oligonucleotide primers consisting of base sequences of SEQ ID NOS: 5 to 8 and the oligonucleotide probes consisting of base sequences of SEQ ID NOS: 11 and 12.

Therefore, the detection kit for determining the patient-derived xenograft cells of the present application may include the oligonucleotide primers consisting of base sequences of SEQ ID NOS: 1 to 8 and the oligonucleotide probes consisting of base sequences of SEQ ID NOS: 9 to 12. In addition, it is possible to measure the ratio of the human albumin genes and the mouse albumin genes the ratio of the human papola genes and the mouse papola genes included in the xenograft cells of the human and the mouse by using the detection kit.

Further, in the present application, it is possible to measure a ratio of the human genes and the mouse genes in the patient-derived xenograft cells by performing a real-time polymerase chain reaction using a polymerase chain reaction (PCR), particularly, a conventional PCR, a real-time PCR, or a droplet digital PCR (dd PCR). In the present invention, the 'polymerase chain reaction' or 'PCR' includes general (non-quantitative) PCR and quantitative PCR, and for example, may be used as a concept including both a general PCR and a real-time PCR or a concept indicating the 'general PCR' depending on the context.

In one example, the concentration of the oligonucleotide probes in the detection kit for determining the patient-derived xenograft cells may be 1 pmol or more, and in this case, it is possible to improve sensitivity in detecting the cross contamination of the patient-derived xenograft cells. For example, in the case of amplifying the genes by using the real-time PCR, the concentration of the oligonucleotide probes may be 1 pmol, and in the case of amplifying the genes by using the dd PCR, the concentration of the oligonucleotide probes may be 5 pmol.

Further, the present application relates to a method for determining cross contamination of mouse genes for human cells by using the aforementioned detection kit.

The method for determining the cross contamination of the present application may be performed by using the aforementioned detection kit and accordingly, the duplicated contents with the contents described in the aforementioned detection kit will be omitted.

An exemplary embodiment of the method for determining cross contamination of mouse genes for human cells of the present application includes amplifying a human albumin gene and a mouse albumin gene using oligonucleotide primers consisting of base sequences of SEQ ID NOS: 1 to 4 by a PCR method; hydrolyzing oligonucleotide probes consisting of base sequences of SEQ ID NOS: 9 and 10; and detecting a labeling means binding to the probes. According to the method for determining cross contamination, it is possible to measure a ratio of the human albumin gene and the mouse albumin gene in a patient-derived xenograft model.

Another exemplary embodiment of the method for determining cross contamination of the present application includes amplifying a human papola gene and a mouse papola gene using oligonucleotide primers consisting of base sequences of SEQ ID NOS: 5 to 8 by a PCR method; hydrolyzing oligonucleotide probes consisting of base sequences of SEQ ID NOS: 11 and 12; and detecting a labeling means binding to the probes. According to the method for determining cross contamination, it is possible to measure a ratio of the human papola gene and the mouse papola gene in a patient-derived xenograft model.

In detail, the method for determining cross contamination of the mouse gene for the human cells may be performed as follows. For example, the method for determining the cross contamination may be configured by including the following seven steps.

1. Preparation of Standard and Control Samples

The present application relates to a method for determining cross contamination using a real-time PCR kit capable of analyzing cross contamination of mouse stromal cells that may be generated in a patient-derived xenograft banking process. To this end, samples in standard and control groups corresponding to each gene were prepared by synthesizing mini genes. In one example, the samples may be obtained from a tissue or a patient-derived tissue (cells) in a patient-derived xenograft model or cell-derived xenograft model.

2. DNA Isolation

DNA was isolated by establishing an appropriate method from various samples obtained in step 1.

3. Single Real-time PCR

Oligonucleotide primers for amplifying a human albumin gene, a mouse albumin gene, a human papola gene, and a mouse papola gene were designed, appropriate real-time PCR conditions were established, the real-time PCR was performed by a single PCR, and each condition was established by varying a concentration ratio of the primer corresponding to each gene.

4. Securing Clones

Clones including DNA segments including each gene were synthesized. The clones were used as the samples in the standard and control groups when the reaction condition of the detection kit of the present application was established.

5. Probe Design

Oligonucleotide probes capable of determining our types of housekeeping genes of the human albumin gene, the mouse albumin gene, the human papola gene, and the mouse papola gene by a hydrolysis reaction in a real-time PCR process were designed.

For example, a target probe binding to the target gene is a Taq Man probe having SEQ ID NOS: 9 to 12 and MGB or BHQ may bind to a 3' terminal.

6. Establishment of Reaction and Analysis Conditions in Real-time PCR Equipment

Mouse and human genes were amplified by the single PCR by setting a standard sample which was obtained by combining one or two of clones for each type obtained in step 4 and composed at various concentrations as a template and analyzed with real-time PCR equipment after performing the hydrolysis reaction to establish appropriate conditions.

7. Analysis of Patient-derived Xenograft Sample Using Real-time PCR Kit

After performing the PCR in step 3, DNA of the patient-derived xenograft sample of which a genotype was confirmed by a sequencing reaction was targeted and analyzed with the real-time PCR equipment after performing the single real-time PCR again. Accordingly, sensitivity, specificity, and reproducibility of the detection kit of the present application were synthesized and an optimal condition for cross contamination analysis was established again.

8. Establishment of Reaction and Analysis Conditions in ddPCR Equipment

Mouse and human genes were amplified by the single PCR by setting a standard sample which was obtained by combining one or two of clones for each type obtained in step 4 and composed at various concentrations as a template and analyzed with ddPCR equipment after performing the hydrolysis reaction to establish appropriate conditions.

9. Analysis of Patient-Derived Xenograft Sample Using ddPCR

After performing the PCR in step 3, DNA of the patient-derived xenograft sample of which a genotype was confirmed by a sequencing reaction was targeted and analyzed with the ddPCR equipment after performing the single real-time PCR again. Accordingly, sensitivity, specificity, and reproducibility of the detection kit of the present application were synthesized and an optimal condition for cross contamination analysis was established again.

Further, in one example, the detection kit including the oligonucleotide probes, the oligonucleotide primers, and the labeling means of the present application may use DNA extracted from a commercial product (a manual method or an automatic method) which is a reagent that extracts the DNA from the sample in the patient-derived xenograft model or cell-derived xenograft model. The detection kit include 1) a reagent related with real-time PCR amplification of four types of the human albumin gene, the mouse albumin gene, the human papola gene, and the mouse papola gene, 2) a plasmid DNA clone to be used as a positive control group when amplifying the genes, and 3) oligonucleotide probes for cross contamination detection, and reactants required for the real-time PCR reaction using the kit.

As a result, in the analysis kit for cross contamination of genes related with the human and the mouse, the detection kit for determining the patient-derived xenograft cells, and the method for cross contamination determination, it is possible to rapidly and accurately analyze cross contamination of mouse genes in the patient-derived xenograft model or cell-derived xenograft model and genotypes thereof and further, quantitatively exhibit the cross contamination of genes related with the human and the mouse through a polymerase chain reaction (PCR).

The present application relates to a detection kit for determining patient-derived xenograft cells and a method for determining cross contamination. According to the present invention, it is possible to determine all of cross contamination of mouse related genes, have high detection sensitivity and specificity to be close to 100%, rapidly examine the contamination, and be very useful in predicting mouse contamination.

Therefore, according to the present invention, cross contamination of genes related with the human and the mouse is predicted in advance to be applied to evaluation of anticancer drug efficacy using a patient-derived xenograft model or cell-derived xenograft model and contribute to cell banks using the patient-derived xenograft model or cell-derived xenograft model, and as a result, the present invention is very useful in a medical industry.

BRIEF DESCRIPTION OF THE DRAWINGS

FIG. 1 is a conventional PCR result of a human albumin gene, a mouse albumin gene, a human papola gene, and a mouse papola gene using miniclones.

FIG. 2 is a conventional PCR result of a human albumin gene, a mouse albumin gene, a human papola gene, and a mouse papola gene using a human gDNA and a mouse gDNA.

FIGS. 3, 4, and 5 are real-time PCR results of a human albumin gene, a mouse albumin gene, a human papola gene, and a mouse papola gene using 0.01 ng of a miniclone of the present invention.

FIGS. 6 and 7 are real-time PCR results of a human albumin gene, a mouse albumin gene, a human papola gene, and a mouse papola gene using a human gDNA and a mouse gDNA of the present invention.

FIG. 8 is a ddPCR result of a human albumin gene and a mouse albumin gene using a miniclone of the present invention.

FIG. 9 is a ddPCR result of a human papola gene and a mouse papola gene using a miniclone of the present invention.

FIG. 10 is a ddPCR result of a human albumin gene and a mouse albumin gene using a human gDNA and a mouse gDNA of the present invention.

FIG. 11 is a ddPCR result of a human papola gene and a mouse papola gene using a human gDNA and a mouse gDNA of the present invention.

FIG. 12 is a real-time PCR result of a human albumin gene and a mouse albumin gene using a gDNA in a patient-derived xenograft model using the same tissue as a patient's tissue of the present invention.

FIG. 13 is a real-time PCR result of a human papola gene and a mouse papola gene using a gDNA in a patient-derived xenograft model using the same tissue as a patient's tissue of the present invention.

FIG. 14 is a ddPCR result of a human albumin gene and a mouse albumin gene using a gDNA in a patient-derived xenograft model using the same tissue as a patient's tissue of the present invention.

FIG. 15 is a ddPCR result of a human papola gene and a mouse papola gene using a gDNA in a patient-derived xenograft model using the same tissue as a patient's tissue of the present invention.

DETAILED DESCRIPTION OF THE PREFERRED EMBODIMENT

Hereinafter, the present application will be described in more detail through exemplary embodiments of the present application, but the scope of the present application is not limited to the following exemplary embodiments.

The present invention relates to a kit and a method for detecting cross contamination that rapidly and accurately analyzes cross contamination of mouse genes which may be generated in an incubation process in a patient-derived xenograft model or a cell-derived xenograft model and is useful even when applying SOP to a patient-derived xenograft model or cell-derived xenograft model banking.

Hereinafter, exemplary embodiments described below can be modified into various other forms and the scope of the present invention is not limited to exemplary embodiments described below. Exemplary embodiments of the present invention will be provided for more completely describing the present invention to those skilled in the art.

1) Preparation of Control Sample and DNA Extraction

In the present invention, DNA was extracted using DNeasy, Blood & Tissue kit (Qiagne, 69506), but in order to perform the technology, the DNA was extracted using a commercial product. A DNA extraction method using the kit is as follows.

① A patient-derived tissue and a patient-derived xenograft or cell-derived xenograft tissue are collected in a centrifuge tube, centrifuged for 5 minutes at 300 Xg, and resuspended well with 200 µl of PBS.

② 20 µl of Proteinas K is added.

③ 200 µl of Buffer AL is added and reacted for 10 minutes at 56° C. after vortexing. 200 µl of Ethanol (96-100%) is added and mixed by vortexing.

④ The mixture is transferred to a DNeasy Mini spin column sticking in a 2 ml collection tube and then centrifuged for 1 minute at 8,000 rpm (the solution filtered by the collection tube is removed).

⑤ The DNeasy Mini spin column is transferred to a new 2 ml collection tube and then added with 500 µl of a buffer AW1 and centrifuged for 1 minute at 8,000 rpm (the solution filtered by the collection tube is removed).

⑥ The DNeasy Mini spin column is transferred to a new 2 ml collection tube and then added with 500 µl of a buffer AW2 and centrifuged for 3 minutes at 14,000 rpm (the solution filtered by the collection tube is removed).

⑦ The DNeasy Mini spin column is transferred to a new 2 ml collection tube and then centrifuged for 1 minute at 14,000 rpm (the solution filtered by the collection tube is removed).

⑧ The DNeasy Mini spin column is transferred to a 1.5 ml or 2 ml clean microcentrifuge tube and then 200 µl of a buffer AE 200 is directly dropped on a DNase membrane. The DNeasy Mini spin column is reacted for 3 minutes at room temperature and then centrifuged at 8,000 rpm.

A criterion for judging the extracted DNA is as follows.

In the case of DNA or RNA, a maximum absorbance is shown at a wavelength of 260 nm, and a UV absorbing radiation amount is proportional to the DNA amount, and thus if the absorbance value at the wavelength of 260 nm is 1.0, the ds-DNA shows a concentration of 50 ug/ml. Accordingly, under the assumption of pure DNA, if the absorbance value at the wavelength of 260 nm is 2.0, the ds-DNA shows a concentration of 100 ug/ml. As a substance that can interfere at a similar wavelength, proteins, phenol, and the like are included, and these substances have a maximum absorbance at a wavelength of 280 nm. As such, when the interfering substance is present, cross contamination with other substances may be confirmed by an absorbance ratio (A260/A280) of the wavelength of 260 nm and the wavelength of 280 nm. In the case of the pure DNA without the interfering substance, the absorbance ratio (A260/A280) of the wavelength of 260 nm and the wavelength of 280 nm has a value of 1.8 or more, and if the value is 2.0, this may be defined as 100% pure DNA (or RNA). If the pure DNA is contaminated with proteins or phenol, the absorbance ratio (A260/A280) of the wavelength of 260 nm and the wavelength of 280 nm has a value of 1.8 or less. In this case, the quantity of the sample may not be accurate. When the absorbance at the wavelength is 1, the ds-DNA has a concentration of 50 µg/ml, the ss-DNA has a concentration of 33 µg/µl, the RNA has a concentration of 40 µg/ml, and the oligomer has a concentration of 25 to 35 µg/ml.

Further, the purity of the extracted DNA needs to be measured in ranges of the A260/A280 ratio of 1.8 to 2.1 and the A260/A230 ratio of 1.5 to 2 or more.

2) Preparation of Standard and Control Samples

A plasmid DNA clone including a human albumin gene, a mouse albumin gene, a human papola gene and a mouse papola gene which are related genes to be standard substances in the genotype analysis was synthesized and prepared.

3) Single Real-time PCR

In order to examine cross contamination that may occur in the incubation process of the patient-derived xenograft model or cell-derived xenograft model, related human and mouse genes were amplified, respectively. For the PCR amplification, oligonucleotide primers were first selected and designed.

The primers created in the present invention were designed by using housekeeping genes that were differentiated according to the human and the mouse.

The primer of the present invention consists of primers (SEQ ID NOS: 1 to 8) that detect four genes of a human albumin gene, a mouse albumin gene, a human papola gene, and a mouse papola gene below and the PCRs of the human albumin and papola genes and the mouse albumin and papola genes amplify products having lengths of 142, 131, 134, and 133 bp, respectively. A base sequence of the PCR primer for each gene was illustrated in Table 1 below.

TABLE 1

| No. | Sequence (5'→3') | Length (mer) | GC (%) | Tm (° C.) | Amplicon Size (bp) | Direction | Gene | Gene Bank No. |
|---|---|---|---|---|---|---|---|---|
| 1 | GGTCTGAGGAGAAA GTGTAGCA | 22 | 50 | 60.2 | 142 | Forward | Human albumin | NG_009291 |
| 2 | CAGAGGTTTTTCAC AGCATTCC | 22 | 45.5 | 58.3 | | Reverse | | |
| 3 | GATTGATAAAGCCA GGGTGAT | 21 | 42.9 | 55.9 | 131 | Forward | Mouse albumin | NC_000071.6 |

TABLE 1-continued

| No. | Sequence (5'→3') | Length (mer) | GC (%) | Tm (° C.) | Amplicon Size (bp) | Direction | Gene | Gene Bank No. |
|---|---|---|---|---|---|---|---|---|
| 4 | ACTGTCACTGTCACTGTCAAGC | 22 | 50 | 60.2 | | Reverse | | |
| 5 | CGTTAGGATATGTGGTAAGCGT | 22 | 45.5 | 58.3 | 134 | Forward | Human papola | NC_000014.9 |
| 6 | ATAAACGCATCCATTACCTCCA | 22 | 40.9 | 56.5 | | Reverse | | |
| 7 | TTCCTGGGTCAAGGTTACTTAG | 22 | 45.5 | 58.3 | 133 | Forward | Mouse papola | NC_000078.6 |
| 8 | AAAGTGATCGCCAGATTCAATG | 22 | 40.9 | 56.5 | | Reverse | | |

4) Probe Design of Kit

Oligonucleotide probes (SEQ ID NOS: 9 to 12) for retrieving genotypes of housekeeping genes selected for designing the oligonucleotide probes of the genes related with the human and the mouse were designed.

The oligonucleotide probes of the present invention were genotype-specific probes capable of specifically binding to each of four genes of the human albumin gene, the mouse albumin gene, the human papola gene, and the mouse papola gene according to an object of the present invention and the oligonucleotide was designed, and the genotype specific probes were designed by using a computer program Pyro-Mark assay design or a primer3 of the ensured DNA sequence.

In this case, the length of the oligonucleotide probe was set to an oligonucleotide of 23±2 bp to primarily design four types of specific probes, and the detection reagent and the kit related with the human and mouse genotypes for detecting the cross contamination of the mouse stromal cells target a total of four genes of the human albumin and papola genes and the mouse albumin and papola genes. For example, the target probe binding to the target gene is a Taq Man probe having SEQ ID NOS: 9 to 12 and MGB or BHQ may bind to a 3' terminal.

The SEQ ID NOs and types of the oligonucleotide probes were summarized in Table 2 below.

5-1) Establishment of Conventional PCR Reaction and Analysis Conditions

The genes related with the human and the mouse were amplified by conventional PCR by setting a clone for each type of the genes related with the human and the mouse established in a single real-time PCR as a template and then electrophoresis was performed to confirm the gene amplification.

Component and conditions for confirming the genotypes of the genes related with the human and the mouse were performed as follows.

Conventional PCR component and condition

1. Component

TABLE 3

| Component | Volume |
|---|---|
| Miniclone (10 ng) | 1 μl |
| Primer mix F, R (10 pmol/ul) | 1 μl |
| LightCycler Probe Master (2×) | 10 μl |
| Water, PCR-grade | 8 μl |
| Total volume | 20 μl |
| gDNA (30 ng) | 1 μl |
| Primer mix F, R (10 pmol/ul) | 1 μl |
| LightCycler Probe Master (2×) | 10 μl |

TABLE 2

| No. | Sequence (5'→3') | Length (mer) | GC (%) | Tm ( ) | Direction | Gene | Gene Bank No. |
|---|---|---|---|---|---|---|---|
| 9 | CCAACTTACTTATAGGCGGACCTTG | 25 | 48 | 62.9 | Reverse | Human albumin | NG_009291 |
| 10 | AAAGTCTCACCACATGACTGCCCAA | 25 | 48 | 62.9 | Reverse | Mouse albumin | NC_000071.6 |
| 11 | AGGTTGCGTGCTCTTATGGCAGAAA | 25 | 48 | 62.9 | Forward | Human papola | NC_000014.9 |
| 12 | TGTTTCTTATGCCTCCATAGGTGGT | 25 | 44 | 61.3 | Forward | Mouse papola | NC_000078.6 |

TABLE 3-continued

| Component | Volume |
|---|---|
| Water, PCR-grade | 8 μl |
| Total volume | 20 μl |

A PCR mixture was prepared as illustrated in Table above.

2. Program

TABLE 4

| Program | Temperature( ) | Hold |
|---|---|---|
| Pre-Incubation | 95 | 5 m |
| Amplification 30 cycles | 95 | 20 s |
|  | 55~65 | 30 s |
|  | 72 | 1 m |
| Cooling | 12 | 30 s |

Each amplicon (PCR product) that was PCR with the above program in a PCR machine and then amplified by electrophoresis was confirmed.

The conventional PCR result of the human albumin gene, the mouse albumin gene, the human papola gene, and the mouse papola gene using the miniclones was illustrated in FIG. 1. The conventional PCR result of the human albumin gene, the mouse albumin gene, the human papola gene, and the mouse papola gene using a human gDNA and a mouse gDNA was illustrated in FIG. 2.

5-2) Establishment of Real-Time PCR Reaction and Analysis Conditions

It was confirmed that the genes related with the human and the mouse were amplified by real-time PCR by setting a clone for each type of the genes related with the human and the mouse established in a single real-time PCR as a template.

Components and conditions of real-time PCR for confirming the genotypes of the genes related with the human and the mouse were performed as follows.

Real-Time PCR Component and Condition

1. Component

TABLE 5

| Component | Volume |
|---|---|
| gDNA (30 ng) | 1 μl |
| Primer mix F, R (10 pmol/ul) | 1 μl |
| Probe (1 pmol/ul) | 1 μl |
| LightCycler Probe Master (2×) | 10 μl |
| Water, PCR-grade | 7 μl |
| Total volume | 20 μl |
| Miniclone (0.01 ng) | 1 μl |
| Primer mix F, R (10 pmol/ul) | 1 μl |
| Probe (1 pmol/ul) | 1 μl |
| LightCycler Probe Master (2×) | 10 μl |

TABLE 5-continued

| Component | Volume |
|---|---|
| Water, PCR-grade | 7 μl |
| Total volume | 20 μl |

2. Program

The PCR was performed in a PCR machine by the following program.

TABLE 6

| Program | Cycles | Analysis mode | temperature( ) | Hold time | Acquisition mode |
|---|---|---|---|---|---|
| Pre-Incubation | 1 | None | 95 | 10 min | None |
| Amplification | 45 | Quantification | 95 | 10 s | None |
|  |  |  | 60 | 30 s | Single |
| Cooling | 1 | None | 40 | 30 s | None |

However, in the probe combination, in the case of the human, FAM was used as the labeling means of the 5' terminal of the oligonucleotide and in the case of the mouse, HEX fluorescence was used as the labeling means of the 5' terminal of the oligonucleotide and MGB and BHQ1 was used as the labeling means of a 3' terminal of the oligonucleotide.

The real-time PCR results of the human albumin gene, the mouse albumin gene, the human papola gene, and the mouse papola gene using 0.01 ng of the miniclone were illustrated in FIGS. 3, 4, and 5. The real-time PCR results of the human albumin gene, the mouse albumin gene, the human papola gene, and the mouse papola gene using a human gDNA and a mouse gDNA were illustrated in FIGS. 6 and 7.

5-3) Establishment of ddPCR Reaction and Analysis Conditions

It was confirmed that the genes related with the human and the mouse were amplified by dd PCR by setting a clone for each type of the genes related with the human and the mouse established in a single real-time PCR as a template.

Components and conditions of ddPCR for confirming the genotypes of the genes related with the human and the mouse were performed as follows.

ddPCR Components and Conditions

1. Component 1.1 In the case of a minigene, a PCR mixture was made as illustrated in Table below.

① Under the conditions illustrated in Table below, a restriction enzyme was added and reacted at 55° C. for 5 minutes.

TABLE 7

| Component | Volume (μl) |
|---|---|
| BseC I (ClaI Isoschizomer) (2 unit/μl) | 10 |
| Minigene (500 ng) | 10 |

② An enzyme digestion product was purified by NeucleoSpin Gel and PCR Clean-up.

③ The test was performed by quantifying Qubit and calculating the copy number by the quantification value.

④ A miniclone PCR mixture was made as illustrated in Table below.

TABLE 8

| Component | Volume (μl) |
| --- | --- |
| Miniclone (2500 copies/μl) | 2.2 |
| Primer Mix 1 (10 pmol/μl) | 1.98 |
| Primer Mix 2 (10 pmol/μl) | 1.98 |
| Probe 1(5 pmol/μl) | 1.1 |
| Probe 2(5 pmol/μl) | 1.1 |
| ddPCR Supermix for Probes | 11 |
| DW | 2.64 |
| Total | 22 |

Note:
Primer final conc. 900 nM, probe final conc. 250 nM 1.2 In the case of a patient-derived xenograft model sample, the extracted gDNA and a PCR mixture were made as illustrated in Table below.

TABLE 9

| Component | Volume (μl) |
| --- | --- |
| gDNA (5 ng/μl) | 2.2 (10 ng) |
| Primer Mix 1 (10 pmol/μl) | 1.98 |
| Primer Mix 2 (10 pmol/μl) | 1.98 |
| Probe 1(5 pmol/μl) | 1.1 |
| Probe 2(5 pmol/v) | 1.1 |
| ddPCR Supermix for Probes | 11 |
| 2 units Hind III | 1.1 |
| DW | 1.54 |
| Total | 22 |

① The gDNA and PDX sample PCR mixture were incubated in RT for 10 minutes to digest Hind III.
② A droplet generator cartridge was mounted on a cartridge holder.
③ 20 ul of the mixture was taken from a 8-Strip PCR tube by using a channel electronic pipette to be loaded in a sample well of the cartridge.
Note: The 8-channel electronic pipette was used by setting the slowest speed.
Note: If 8 sample loading wells of the cartridge were not fully filled, a 2×ddPCR Super Mix and DW were mixed at 1:1 in the rest of the loading wells to be filled by 20 μl.
④ Droplet generation oil was loaded in an oil loading well of the cartridge by 70 μl.
⑤ The droplet generation oil was mounted by dividing the top and the bottom of a droplet generator gasket and put in a QX200™ droplet generator and operated to generate a droplet.
⑥ The generated droplet was transferred to a 96-well plate by 40 μl by using a 8-channel multi-pipette.
A pierceable foil heat seal (BIO-RAD, 181-4040) was covered on the plate with a red line down and put in a PX1™ PCR plate sealer (180° C., sealing for 5 sec) to seal the plate.
2. Program
The PCR was performed in a digital PCR machine by the following program.

TABLE 10

| Program Name | Cycles | Temperature Target (° C.) | Hold time | Ramp Rate |
| --- | --- | --- | --- | --- |
| Enzyme Activation | 1 | 95 | 10 min | ~2° C./sec |
| Denaturation | 40 | 94 | 30 s | |
| Annealing/Extension | | 58 | 1 min | |
| Enzyme deactivation | 1 | 98 | 10 min | |
| Hold (optional) | 1 | 4 | Infinite | |

However, in the probe combination, in the case of the human, HEX fluorescence was used as the labeling means of the 5' terminal of the oligonucleotide and in the case of the mouse, FAM fluorescence was used as the labeling means of the 5' terminal of the oligonucleotide and MGB and BHQ1 was used as the labeling means of a 3' terminal of each oligonucleotide.

The ddPCR result of the human albumin gene and the mouse albumin gene using the miniclone was illustrated in FIG. 8, and the ddPCR result of the human papola gene and the mouse papola gene using the miniclone was illustrated in FIG. 9. The ddPCR result of the human albumin gene and the mouse albumin gene using the human gDNA and the mouse gDNA was illustrated in FIG. 10, and the ddPCR result of the human papola gene and the mouse papola gene using the human gDNA and the mouse gDNA was illustrated in FIG. 11.

6) Analysis of Clinical Sample (e.g., Tissue Sample of Patient Before Making Pt:PDX) Using Hu-Mo ID Kit and PDX Sample (dP. P0: PDX 0-Generation Sample, P1: PDX 1-Generation Sample)

According to the method described in the establishment of the 5-2) real-time PCR reaction and analysis condition and the establishment of the 5-3) ddPCR reaction and analysis condition, a clinical sample and the same tissue were implanted and analyzed by performing real-time PCR and ddPCR using the tissue of a patient-derived xenograft model obtained by performing a subculture.

The real-time PCR result of the human albumin gene and the mouse albumin gene using the gDNA in the patient-derived xenograft model using the same tissue as the patient's tissue was illustrated in FIG. 12, and the real-time PCR result of the human papola gene and the mouse papola gene using the gDNA in the patient-derived xenograft model using the same tissue as the patient's tissue was illustrated in FIG. 13.

As illustrated in FIG. 12, in PDX002-Pt (patient 002), the human albumin gene was 29.91 and the mouse albumin gene was 35.26, in PDX002-P0 (PDX 0 generation of patient 002), the human albumin gene was 27.56 and the mouse albumin gene was 25.68, and in PDX002-1-1-P1 (PDX 1 generation of patient 002), the human albumin gene was 27.34 and the mouse albumin gene was 26.59. Further, in PDX005-Pt (patient 005), the human albumin gene was 29.96, and in PDX005-1-P0 (PDX 0 generation of patient 005), the human albumin gene was 27.77 and the mouse albumin gene was 28.24. That is, the result represents the human albumin gene and the mouse albumin gene as the generation proceeds in the patient-derived xenograft model, and as a result, the cross contamination degree of the mouse-derived tissue may be determined.

As illustrated in FIG. 13, in PDX002-Pt (patient 002), the human papola gene was 29.17, in PDX002-P0 (PDX 0 generation of patient 002), the human papola gene was 27.21 and the mouse papola gene was 27.01, and in PDX002-1-1-P1 (PDX 1 generation of patient 002), the human papola gene was 27.17 and the mouse papola gene was 27.99. Further, in PDX005-Pt (patient 005), the human papola gene was 28.75, and in PDX005-1-P0 (PDX 0 generation of patient 005), the human papola gene was 26.83 and the mouse papola gene was 29.58. That is, the result represents the human papola gene and the mouse papola gene as the generation proceeds in the patient-derived xenograft model, and as a result, the cross contamination degree of the mouse-derived tissue may be determined.

The ddPCR result of the human albumin gene and the mouse albumin gene using the gDNA in the patient-derived xenograft model using the same tissue as the patient's tissue was illustrated in FIG. 14, and the ddPCR result of the human papola gene and the mouse papola gene using the gDNA in the patient-derived xenograft model using the same tissue as the patient's tissue was illustrated in FIG. 15.

As illustrated in FIG. 14, in PDX002-Pt (patient 002), the human albumin gene was 84, in PDX002-P0 (PDX 0 generation of patient 002), the human albumin gene was 288 and the mouse albumin gene was 410, and in PDX002-1-1-P1 (PDX 1 generation of patient 002), the human albumin gene was 396 and the mouse albumin gene was 208. Further, in PDX005-Pt (patient 005), the human albumin gene was 102, and in PDX005-1-P0 (PDX 0 generation of patient 005), the human albumin gene was 336 and the mouse albumin gene was 68. That is, the result represents the human albumin gene and the mouse albumin gene as the generation proceeds in the patient-derived xenograft model, and as a result, the cross contamination degree of the mouse-derived tissue may be determined.

Further, as illustrated in FIG. 15, in PDX002-Pt (patient 002), the human papola gene was 106, in PDX002-1-P0 (PDX 0 generation of patient 002), the human papola gene was 236 and the mouse papola gene was 388, and in PDX002-1-1-P1 (PDX 1 generation of patient 002), the human papola gene was 290 and the mouse papola gene was 202. Further, in PDX005-Pt (patient 005), the human papola gene was 84, and in PDX005-1-P0 (PDX 0 generation of patient 005), the human papola gene was 392 and the mouse papola gene was 60. That is, the result represents the human papola gene and the mouse papola gene as the generation proceeds in the patient-derived xenograft model, and as a result, the cross contamination degree of the mouse-derived tissue may be determined.

What is claimed is:

1. A detection kit that determines patient-derived xenograft cells, comprising: oligonucleotide primers consisting of base sequences of SEQ ID NOS: 9 and 10 and oligonucleotide probes consisting of base sequences of SEQ ID NOS: 9 and 10 and an attached label, wherein the primers and the probes determines a ratio of genes included in xenograft cells of a human and a mouse.

2. The detection kit of claim 1, further comprising: oligonucleotide primers consisting of base sequences of SEQ ID NOS: 5 to 8, and oligonucleotide probes consisting of base sequences of SEQ ID NOS: 11 and 12 and an attached label, wherein the detection kit measures a ratio of a human papola gene and a mouse papola gene included in xenograft cells of a human and a mouse.

3. The detection kit of claim 1, wherein the concentration of the oligonucleotide probes is 1 pmol or more.

4. A method for determining cross contamination of mouse genes for human cells in a method for determining patient-derived xenograft cells, the method comprising the steps of: amplifying a human albumin gene and a mouse albumin gene by using oligonucleotides primers consisting of base sequences of SEQ ID NOS: 1 to 4 by a PCR method; hydrolyzing oligonucleotide probes consisting of base sequences of SEQ ID NOS: 9 and 10 ; and detecting binding of the probes and determining a ratio of the human albumin gene and the mouse albumin gene to determine cross contamination.

5. The method of claim 4, wherein the concentration of the oligonucleotide probes is 1 pmol or more.

6. The method of claim 4, wherein the PCR method is any one selected from a conventional PCR, a real-time PCR, or a droplet digital PCR (ddPCR).

* * * * *